(12) United States Patent
Schroeder

(10) Patent No.: US 7,274,447 B2
(45) Date of Patent: Sep. 25, 2007

(54) MATERIAL POROSITY PRESSURE IMPULSE TESTING SYSTEM

(75) Inventor: Terrence K. Schroeder, Bernardsville, NJ (US)

(73) Assignee: SWCE, Bernardsville, NJ (US)

( * ) Notice: Subject to any disclaimer, the term of this patent is extended or adjusted under 35 U.S.C. 154(b) by 287 days.

(21) Appl. No.: 10/872,899

(22) Filed: Jun. 21, 2004

(65) Prior Publication Data

US 2005/0279948 A1 Dec. 22, 2005

(51) Int. Cl.
*G01N 21/00* (2006.01)
*G01J 1/58* (2006.01)
*C12Q 1/68* (2006.01)

(52) U.S. Cl. ............ 356/338; 250/458.1; 435/6; 435/287.2

(58) Field of Classification Search ........ 356/335–343; 250/474.1, 458.1, 583, 252.1, 582, 440.11; 436/148, 518; 435/6, 7.1, 288.4, 288.7; 428/304; 702/27

See application file for complete search history.

(56) References Cited

U.S. PATENT DOCUMENTS

| | | | | |
|---|---|---|---|---|
| 4,243,753 A | * | 1/1981 | Regnier et al. | 435/288.6 |
| 4,672,841 A | * | 6/1987 | Schuster et al. | 73/38 |
| 4,842,406 A | * | 6/1989 | VonBargen | 356/336 |
| 5,116,759 A | * | 5/1992 | Klainer et al. | 435/287.2 |
| 5,138,871 A | * | 8/1992 | Retta et al. | 73/38 |
| 5,496,629 A | * | 3/1996 | Tallentire et al. | 428/304.4 |
| 5,576,480 A | * | 11/1996 | Hopkins et al. | 73/38 |
| 6,197,575 B1 | * | 3/2001 | Griffith et al. | 435/288.4 |
| 6,781,143 B2 | * | 8/2004 | Shimizu et al. | 250/583 |
| 6,989,542 B2 | * | 1/2006 | Moses et al. | 250/440.11 |
| 2002/0110921 A1 | | 8/2002 | Louwen et al. | |
| 2002/0147551 A1 | | 10/2002 | Gupta et al. | |
| 2002/0168665 A1 | * | 11/2002 | Okawa | 435/6 |

OTHER PUBLICATIONS

Standard Test Method for Dye Penetration of Solid Fiberglass Reinforced Pultruded Stock, ATSM International, Designation: D 5117-03, Jan. 2003 pp. 1-3.
Standard Test Methods for Void Content of Reinforced Plastics, ATSM International, Designation: D 2734-94 (Reapproved 2003), Mar 2003 pp. 1-3.
Characterization of Water Vapor Permeable Membranes Akshaya Jena and Krishna Gupta. Desalination, vol. 149, 2002, pp. 471-476.
Use Of Multiple Test Techniques For Evaluation Of Complex Pore Structure Akshaya Jena and Krishna Gupta. AFS 15th Annual Technical Meeting, 2002.

(Continued)

*Primary Examiner*—Sang H. Nguyen
(74) *Attorney, Agent, or Firm*—Mathews, Shepherd, McKay & Bruneau, P.A.

(57) ABSTRACT

A system and method for determining porosity of a material enables rapid testing of materials by detecting test particle penetration. The material is held by a test chamber wherein a test particle solution covers a surface of the material. The test chamber is pressurized to a predetermined pressure, predetermined temperature and for a predetermined time. After the pressure is released the test particle penetration/diffusion into the material is then detected through differential fluorescence of the test particle.

20 Claims, 3 Drawing Sheets

OTHER PUBLICATIONS

Liquid Extrusion Techniques For Pore Structure Evaluation Of Nonwovens Akshaya Jena and Krishna Gupta. International Nonwovens Journal, Fall, 2003, pp. 45-53.

Porous Materials, Inc., Sales Phamplet, "Gas Permeater", pp. 1-2, 20 Dutch Mill Road, Ithaca, NY 14850, USA, first obtained Mar. 2004.

Porous Materials, Inc., Sales Phamplet, "Clamp-On Porometer", pp. 1-2, 20 Dutch Mill Road, Ithaca, NY 14850, USA, first obtained Mar. 2004.

Porous Materials, Inc., Sales Phamplet, "Capillary Flow Porometer", pp. 1-4, 20 Dutch Mill Road, Ithaca, NY 14850, USA, first obtained Mar. 2004.

Porous Materials, Inc., Sales Phamplet, "Liquid Extrusion Porosimeter", pp. 1-2, 20 Dutch Mill Road, Ithaca, NY 14850, USA, first obtained Mar. 2004.

Porous Materials, Inc., Sales Phamplet, "Bubble Point Tester", pp. 1-2, 20 Dutch Mill Road, Ithaca, NY 14850, USA, first obtained Mar. 2004.

* cited by examiner

MATERIAL POROSITY PRESSURE IMPULSE TESTING SYSTEM

FIELD OF INVENTION

The present invention relates to material testing and more particularly to the measurement of porosity.

BACKGROUND OF THE INVENTION

Conditioned environmental chambers are used to protect sensitive equipment including various electronic modules from corrosive materials. A hermetically sealed chamber is typically made from titanium or stainless steel. As the volume of equipment and electronic modules increased over time it was necessary to use larger chambers. In a fixed ground position, the extra weight of the large metal chambers was not a significant concern.

Recent applications of sensitive equipment and electronic modules to marine applications make the use of a titanium or stainless steel chamber less than desirable. Composite materials, such as polyester resins or vinyl resins reinforced with glass elements (fiberglass) or carbon fiber are well suited for this use because of their lightweight, ease of manufacturing and flexibility in configurations. Some of the composites are heavily doped with bromide as a fire retardant. When designed for this use, the composites are designed to have a very low level of porosity, being comprised of layers to build them up to the necessary thickness.

Methods and devices for measuring porosity of materials are well known. Unfortunately, they are essentially designed to measure a flow through a porous material rather than a material designed to have a very low level of porosity. The ASTM Standard Test Method For Dye Penetration Of Solid Fiberglass Reinforced Pultruded Stock, Designation: D 5117-03 published in January 2004 is an example of the types of measurements that are made. In this case a dye penetrant test method is used to evaluate solid fiberglass reinforced pultruded rod stock for longitudinal wicking. The specimen being tested is placed on end into the dye penetrant to a specified depth and wicking due to capillary action of the penetrant is observed. This test does not determine porosity of a material and is not suited for testing of porosity perpendicular to the reinforcing fiber.

U.S. Patent Application Publication No. US 2002/0147551 A1 entitled Pore Structure Analysis Of Individual Layers of Multi-layered Composite Porous Materials discloses a method of determining porosity of a multi layered porous material by measuring the flow through the material under pressure. The method uses an indirect calculation and requires that flow through the material occur and be measurable by displacement.

Conventional quantitative methods (ASTM D 5117-03) requires the use of a fume hood to extract and exhaust potentially irritating vapors during the working process. Other tests involve UV radiation and thus require protective eyewear.

Therefore, there is a need for measuring porosity of a material designed to have a very low level of porosity which does not require measurement of the flow of a gas or liquid through the material under test.

There is further a need for measuring porosity of a material designed to have a very low level of porosity which does not require use of irritating vapors or harmful UV radiation.

SUMMARY OF THE INVENTION

The present invention is a system and method for determining porosity of a material. The material is held by a test chamber wherein a test particle solution covers a surface of the material. The test chamber is pressurized to a predetermined pressure and for a predetermined time. The test particle penetration into the material is then detected.

BRIEF DESCRIPTION OF THE DRAWINGS

A more complete understanding of the present invention may be obtained from consideration of the following description in conjunction with the drawings in which.

DETAILED DESCRIPTION OF VARIOUS ILLUSTRATIVE EMBODIMENTS

Figure 1:
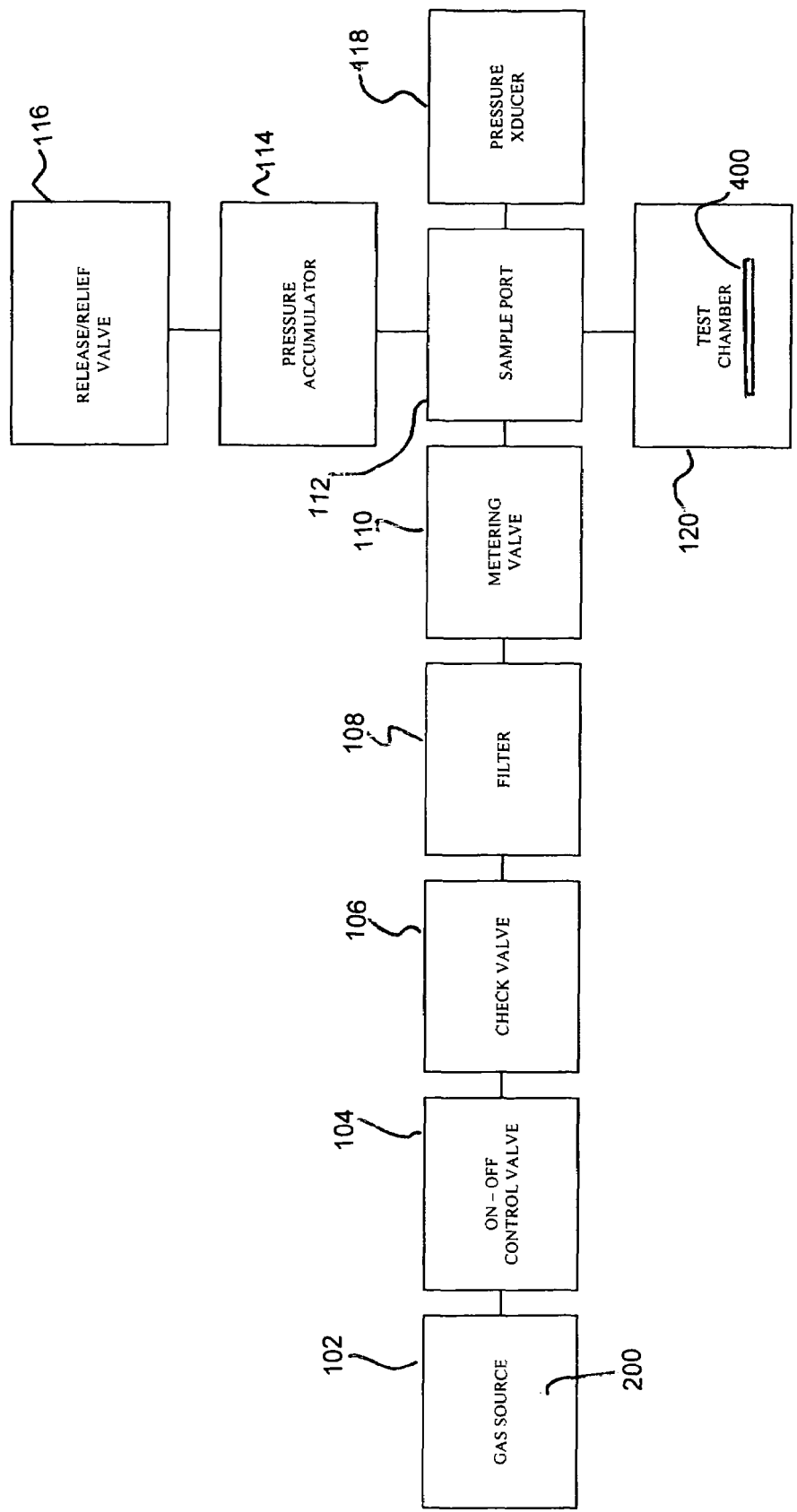
FIG. 1 is a functional block diagram of the material porosity pressure impulse testing system used to apply the test particles to the material.
Figure 2:
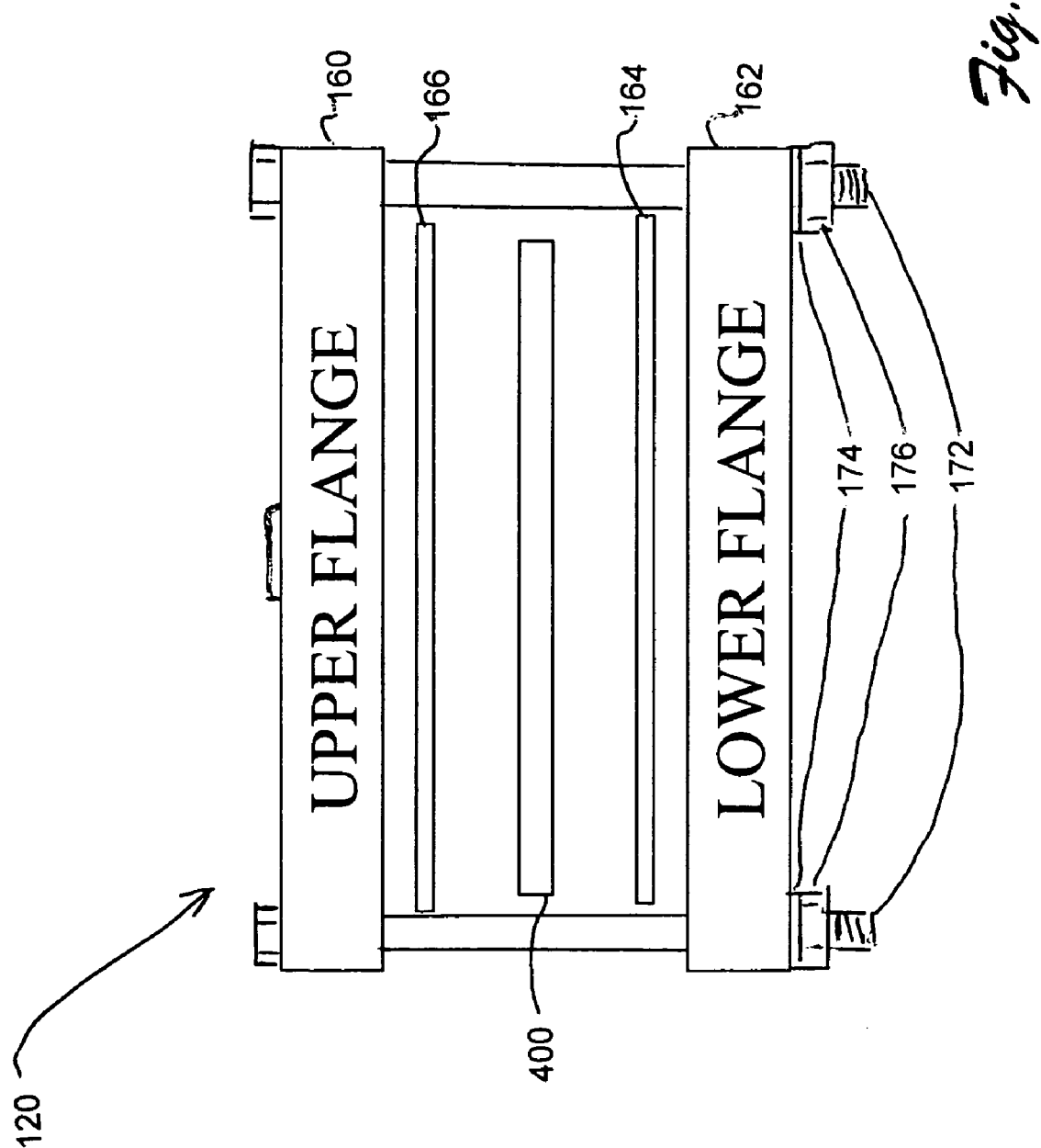
FIG. 2 is a more detailed representation of the test chamber.

Although the present invention material porosity pressure impulse testing system is particularly well suited for determining test particle penetration into a material having a very low level of porosity, and is so described, it is equally well suited for use in determining test particle adhesion to a test material surface having non-porous irregularities and surface voids. The susceptibility of a test material to a test particle/ion includes penetration and diffusion.

Although the present invention material porosity pressure impulse testing system is particularly well suited for testing composite materials and is so described, it is equally well suited for testing of coatings, woods, metals and other materials.

A conditioned environmental console (chamber) can be used to house, contain, cool and hermetically seal the contents to preclude halide migration into various electronic modules contained therein. The conditioned environmental console is made from a composite material having a low level of porosity.

Corrosion caused by the infiltration of halides and moisture into the chamber will destroy the various electronic modules. Corrosion rates vary in proportion to humidity levels and concentration of halides (such as chloride, bromide and iodide) proximal to the corrosion site. Sea water, both liquid and in vapor, is a prime source for these corrosion accelerators.

Barrier mechanisms may be constructed in a composite material, may be a coating for application to the composite material, or a combination of both. To determine the effectiveness of such barrier mechanisms, at best prior methods of evaluation are qualitative rather than quantitative. Some of the procedures require weeks and months in order to test the composite material.

The operating environment of the conditioned environmental console includes internal temperatures from 68 to 122 degrees F. with a relative humidity level of approximately 35%. Externally it is subject to encrustation from 0.7 molar seawater at temperatures from −20 to 140 degrees F. with a relative humidity of 100%. Pressure profiles can include short duration impulse load, such as overpressure from an airburst detonation as well as longer period load cycles.

The conditioned environmental console can be made from composite materials. The composite materials used for the skins or panels are usually produced from parallel laminar layers. The measurement of moisture/fluid penetration is made parallel to the laminare, which is known as wicking (refer to ASTM Standard D 5117-03). No contribution from intra/inter laminar flow, perpendicular to the laminar layers, is measured by the wicking procedure. For an external to internal flow of fluid, as would be the case for the conditioned environment console, this perpendicular flow would be the primary mechanism of ingress.

Flow perpendicular to the laminar layers is most likely caused by the existence of porosity and voids approaching near-molecular size. This mechanism has been substantiated in catalyst research and applies to both coatings and the composites that are coated. This mechanism is the primary source of halide contamination to the conditioned environmental console. The ability to quantify the effect of this mechanism under varying pressures, temperatures and humidity levels can provide significant correlations between measured values and the structural/mechanical properties of the materials tested.

The present invention material porosity pressure impulse testing system provides a portable testing platform which permits testing of a variety of materials under variable temperature, pressure and time profiles, providing quantitative results. The present invention provides a very high linear resolution of rates of penetration and porosity.

The present invention material porosity pressure impulse testing system makes this measurement by determining the distance a test particle travels over a finite time, a finite pressure, and predetermined temperature. The penetration of the test particle is a function of the work (pressure over time) that is applied to the test material.

The selection criteria, for the test particles, was based on size, solubility, detectability, toxicity and cost. The size is based for the type of coatings and composites, which for the conditioned environmental console would have a kinetic diameter proximal to 1000 picometers. The test particle was chosen to be water soluble, although other solvents can be used provided they do not adversely affect the test material. Detectability was chosen for fluorescence with visible light using light microscopy resolved at or below 0.3 micron in linear distance. Additionally the test particle and solvent should be non-toxic and relatively low in cost.

This criteria resulted in the selection of two test particles, Rhodamine B Base and the Disodium Salt of Fluorescein, although other particles are equally well suited and would be known to those skilled in the art. Rhodamine B Base and the Disodium Salt of Fluorescein both have high quantum yields (the ratio of energy absorbed to the energy re-emitted), a kinetic diameter proximal to 1000 picometers, are soluble in water and may be readily excited and observed with light from the visible spectrum (thus eliminating the need for UV radiation). The molecular weight of Rhodamine B Base is 442.56 and of Disodium Salt of Fluorescein is 376.28. Both are non-toxic and Disodium Salt of Fluorescein is biodegradable. They are one of the smallest indicators which are compatible with light microscopy. The majority of pores for the test materials are in this size range. Smaller test particles can be used but alternative methods of detection would be necessary.

The gas source is selected predicated on the specific sample requirements. In general Argon, Helium, Nitrogen and dried compressed air are suitable. To preclude sample contamination and potential reaction, the selected gas should be chemically inert with respect to the test material, free of oil mist or vapor and free of water vapor.

An exemplary embodiment of the present invention material porosity pressure impulse testing system used to apply the test particles to the material is shown in a functional diagram in FIG. 1. The material porosity pressure impulse testing system is comprised of a gas source 102 which is fluidly coupled to an on-off control valve 104. A check valve 106 is fluidly coupled between the on-off control valve 104 and a filter 108. A metering valve 110 is fluidly coupled between the filter 108 and a sample port 112. A pressure accumulator 114 is fluidly coupled between the sample port 112 and a release/relief valve 116. A pressure transducer 118 is coupled to the sample port 112. Test chamber 120 is fluidly coupled to the sample port 112. During operation gas source 102 contains gas 200, sample port 112 contains the test particle in solution 300, and the test chamber 120 contains the test material 400.

The operation of the material porosity pressure impulse testing system involves a series of steps. Initial instrument calibration is determined. A smooth metal plate, the calibration test material 400, of suitable size for the test chamber 120 is inserted between test chamber upper flange gasket 166 and test chamber lower flange gasket 164. The upper flange 160 and lower flange 162 are brought into compressive contact by tightening flange bolts 172, lock washers 174 and nuts 176. The assembled test chamber 120 is then fluidly coupled to the sample port 112. If a test is to be conducted under a variable temperature profile, sample test chamber 120 heating elements (not shown) and profile controller (not shown) are turned on and the programmed temperature profile made ready for execution. The on-off control valve 104 is verified to be in the closed position. The gas source 102 is opened. The metering valve 110 is closed and the pressure transducer 118 output is zeroed.

To perform the calibration the on-off valve 104 is opened. The metering valve 110 is opened full. When the output of the pressure transducer 118 peaks the on-off control valve 104 is closed. Now the metering valve 110 is fully closed. The pressure and temperature are tracked over time for a selected duration and plotted or displayed. The release valve 116 is opened returning the sample port internal pressure to atmospheric pressure. The metering valve 110 is also opened fully.

The calibration test in next run using the required/desired shape of the pressure impulse to be used for the material testing, using varying metering valve and pressure accumulator combinations.

Now the present invention is ready to be run on the test material. A sample of the test material 400 is cut to suitable dimensions for the test chamber 120, inserted between the flange gaskets 164 and 166. The upper flange 160 and lower flange 162 are brought into compressive contact by tightening flange bolts 172; lock washers 174 and nuts 176. The assembled test chamber 120 is then fluidly coupled to the sample port 112. The pressure accumulator 114 and release/relief valve 116 are disconnected from the sample port 112.

A standardized volume/concentration solution 300 containing the test particles is placed on top of the sample in the test chamber by inserting a pipette containing a predetermined volume through the sample port. One embodiment used a 40 ppm concentration which is the minimum suitable for Disodium Salt of Fluorescein with a 1 inch diameter test opening wherein 1 ml of the solution 300 produced a monolayer at the surface of the test material 400. The actual concentration of the solution 300 can be adjusted up to saturation. The pressure accumulator 114 and release/relief valve 116 assembly are reconnected to the sample port. The on-off control valve 104 is verified in the closed position. The gas source 102 is opened. The metering valve 110 is already pre-set from the prior calibration procedure. If the actual test is to be conducted under a variable temperature profile, than the sample test chamber 120 heating elements and profile controller are turned on and programmed profile ready for execution. The pressure transducer 118 output is zeroed. The on-off control valve 104 is opened. When the pressure sensed peaks, the on-off control valve 104 is closed. If the test is being conducted under a variable temperature profile, the programmed temperature profile execution is activated. The pressure, temperature and time are tracked and a plot or display generated for the selected test duration. The release/relief valve 116 is opened to return the internal sample port 112 pressure to atmospheric pressure.

The application of the high-pressure gas 200 to the test particle in solution 300 has now caused the test particles to penetrate the test material 400. The test material 400 sample is removed from the test chamber 120 by loosening flange bolts 172, lock washers 174 and nuts 176. Residual test particle in solution 300 can be washed from the surface and the test material 400 dried.

The typical pressure ranges are from 0 PSI to 3000 PSI with temperature ranges from −30 F to 400 F. Typical operational time durations are from 1 hour to 24 hours. The ranges are dependent on the material characteristics being tested.

Figure 3:
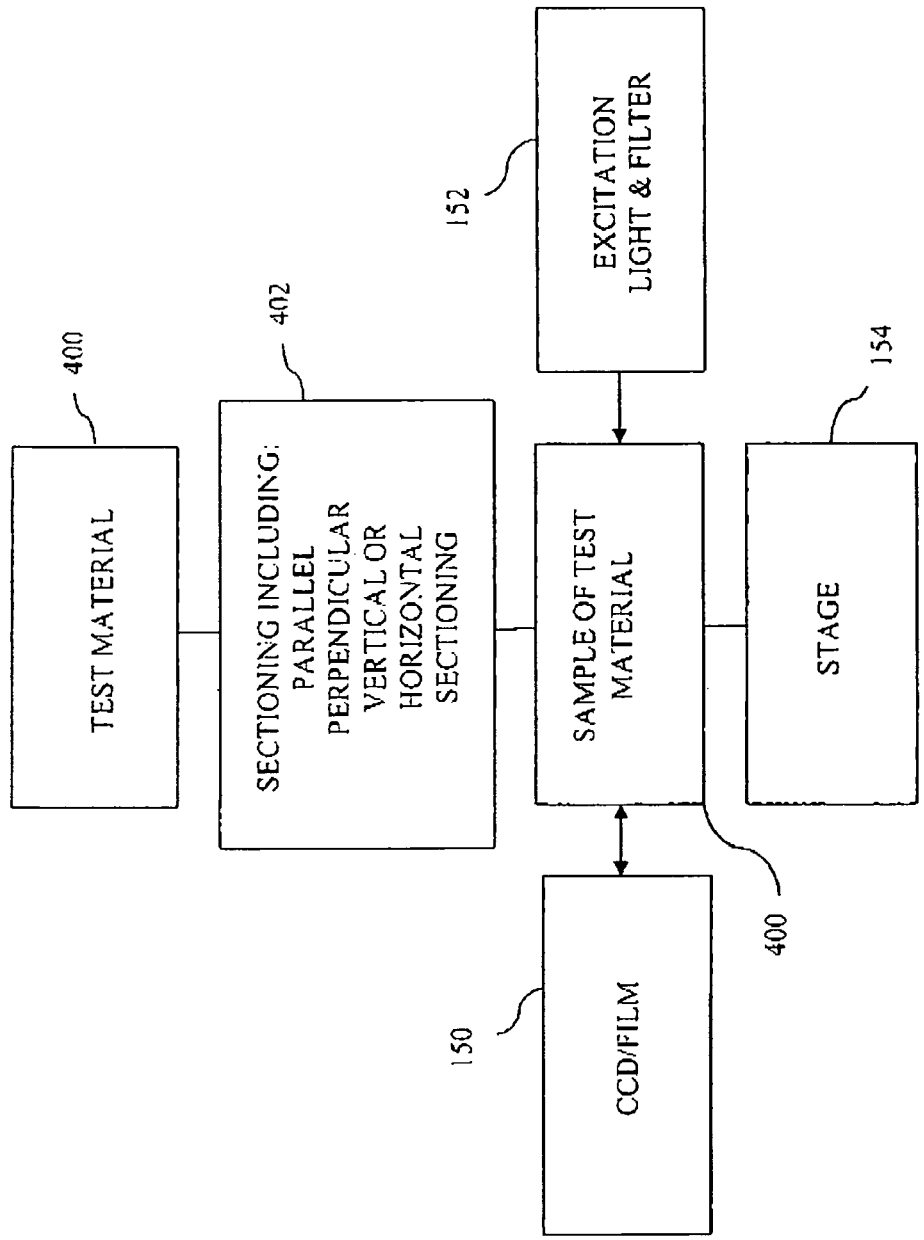
FIG. 3 is a functional block diagram of a detector to determine test particle penetration into the material.

Referring now to FIG. 3, the test material 400 is placed on the automated stage assembly 154 for "breakthrough" examination. Alternatively, the sample can be sectioned 402 either parallel to the laminar structure providing slices for area measurements or sectioned perpendicular to the laminar structure providing cross sections for rate measurement and determination of migration extent. Excitation light and filter 152 causes the rest particles to fluoresce which can then be detected using a CCD device 150. As a further alternative, sample can be sectioned 402 either horizontally or vertically prior to the detecting fluoresce with the CCD device.

Quantitative results for both breakthrough and penetration rates are determined by scanning the test material 400 by using the CCD device 150, suitably calibrated for energy intensity/time, or photographically and then scanning the developed emulsion with a densitometer.

The scanning/sampling sequence uses random location selection determined by random number generation, which is a technique known to those skilled in the art in sampling a surface. The actual pore size and distribution can be determined.

Essentially we are measuring the differential fluorescence (over background fluorescence) of the test particle which has penetrated the test material. The present invention material porosity pressure impulse testing system does not rely on a "event" such as actual flow or bubble through the test material. The scanning can be used to determine the test material porosity for the application of a known pressure over a predetermined time. Variations can include impulse testing, modulation of pressure and temperature.

A pressure spike or multiple pressure spikes can be applied simulating airbursts of explosives. Periodic flexural characteristic effects can also be tested applying a periodic oscillating pressure.

The present invention material porosity pressure impulse testing system can be operated in several different modes. By utilizing a suitable adapter precluding flow parallel to the sample and providing a top flange gasket 166 and the bottom flange gasket 164 with the same size and shape opening, such as a 1 inch circle, we can determine the porosity of the test material 400 uniquely in the Z axis (perpendicular to the surface). We can also measure the cone of movement (Z, X and Y axis) of the test particle through the sample material 400 which includes the X-Y axis (parallel to the surface). By using a solid bottom flange gasket 164 and a smaller opening in the top flange gasket 166 we can measure primarily the X-Y movement of the test particle.

Numerous modifications and alternative embodiments of the invention will be apparent to those skilled in the art in view of the foregoing description. The test chamber 120 may use a variety to methods to achieve compression, including spring force, weight, and may be adapted to testing materials periodically over time. Accordingly, this description is to be construed as illustrative only and is for the purpose of teaching those skilled in the art the best mode of carrying out the invention. Details of the structure may be varied substantially without departing from the spirit of the invention and the exclusive use of all modifications, which come within the scope of the appended claims, is reserved.

I claim:

1. A method of determining porosity of a test material, comprising the steps of:
   positioning the test material in a test chamber;
   applying a test particle solution to cover the test material surface;
   pressurizing the test chamber at a predetermined pressure for a predetermined time;
   detecting test particle penetration of test particles in the test particle solution into the test material by differential fluorescence of the test particles within the test material.

2. The method of determining porosity of a test material as recited in claim 1 wherein the step of detecting further comprises statistically relevant randomized sampling of the test material surface.

3. The method of determining porosity of a test material as recited in claim 1 wherein the test particle in solution is Rhodamine B Base.

4. The method of determining porosity of a test material as recited in claim 1 wherein the test particle in solution is Disodium Salt of Fluorescein.

5. The method of determining porosity of a test material as recited in claim 1 wherein the step of detecting further comprises using a CCD device to scan the test material surface.

6. The method of determining porosity of a test material as recited in claim 1 wherein the step of detecting further comprises using a photographic emulsion to capture an image of the test material surface for density analysis.

7. The method of determining porosity of a test material as recited in claim 1 further comprising the step of sectioning the test material prior to the step of detecting.

8. The method of determining porosity of a test material as recited in claim 7 wherein the step of sectioning the test material further comprises sectioning laminae perpendicular to the test material.

9. The method of determining porosity of a test material a recited in claim 7 wherein the step of sectioning the test material further comprises sectioning laminae parallel to the test material.

10. The method of determining porosity of a test material as recited in claim 1 further comprising the step illuminating die test material surface with visible light for detecting.

11. A system for determining porosity of a test material, the system comprising:

a test chamber for holding the test material having a test particle solution covering the top test material surface;

a means for pressurizing the test chamber to a predetermined pressure for a predetermined time; and a detector, wherein the detector measures test particle penetration of test particles in the test particle solution into the test material by differential fluorescence of the test particles within the test material.

12. The system for determining porosity of a test material as recited in claim 11 wherein the detector uses randomized sampling of the test material surface.

13. The system for determining porosity of a test material as recited in claim 11 wherein the test particle solution is Rhodamine B Base.

14. The system for determining porosity of a test material as recited in claim 11 wherein the test particle solution is Disodium Salt of Fluorescein.

15. The system for determining porosity of a test material as recited in claim 11 wherein the detector further comprises a CCD device for scanning the test material surface.

16. The system for determining porosity of a test material as recited in claim 11 wherein the detector further comprises a photographic emulsion to capture an image of the test material surface for density analysis.

17. The system for determining porosity of a test material as recited in claim 11 further comprising a means for sectioning the test material prior to detecting.

18. The system for determining porosity of a test material as recited in claim 17, wherein the means for sectioning comprises a means for horizontally sectioning the test material prior to detecting.

19. The system for determining porosity of a test material as recited in claim 17, wherein the means for sectioning comprises a means for vertically sectioning the test material prior to detecting.

20. The system for determining porosity of a test material as recited in claim 11 wherein the detector uses visible light.

* * * * *